(12) United States Patent
Franz et al.

(10) Patent No.: US 7,067,148 B2
(45) Date of Patent: Jun. 27, 2006

(54) STABILIZED PHARMACEUTICAL AND THYROID HORMONE COMPOSITIONS AND METHOD OF PREPARATION

(75) Inventors: G. Andrew Franz, St. Louis, MO (US); Elaine A. Strauss, Seminole, FL (US); Philip A. DiMenna, St. Petersburg, FL (US); Rocco L. Gemma, Dover, OH (US)

(73) Assignee: King Pharmaceutical Research & Development, Inc., Cary, NC (US)

( * ) Notice: Subject to any disclaimer, the term of this patent is extended or adjusted under 35 U.S.C. 154(b) by 0 days.

(21) Appl. No.: 10/076,999

(22) Filed: Feb. 15, 2002

(65) Prior Publication Data

US 2003/0119911 A1    Jun. 26, 2003

Related U.S. Application Data

(60) Provisional application No. 60/269,009, filed on Feb. 15, 2001.

(51) Int. Cl.
  *A61K 9/20*    (2006.01)
  *A61K 9/44*    (2006.01)

(52) U.S. Cl. .................. 424/464; 424/465; 424/467
(58) Field of Classification Search ............. 514/567; 424/464, 465, 467
  See application file for complete search history.

(56) References Cited

U.S. PATENT DOCUMENTS

| | | | |
|---|---|---|---|
| 2,426,643 A | 9/1947 | Ridgway | |
| 2,436,005 A | 2/1948 | Hopps et al. | |
| 2,579,668 A | 12/1951 | Hems et al. | |
| 2,642,426 A | 6/1953 | West et al. | |
| 2,705,726 A | 4/1955 | Sydney | |
| 2,802,869 A | 8/1957 | Montgomery | |
| 2,823,164 A | 2/1958 | Pitt-Rivers et al. | |
| 2,866,738 A | 12/1958 | Pasquale et al. | |
| 2,993,928 A | 7/1961 | Razdan et al. | |
| 3,035,974 A | 5/1962 | Israel et al. | |
| 3,380,818 A | 4/1968 | Smith | |
| 3,452,599 A | 7/1969 | Kishel | |
| 3,666,854 A | 5/1972 | Elsentraut et al. | |
| 3,808,332 A | 4/1974 | Reynolds | |
| 3,826,767 A | 7/1974 | Hoover et al. | |
| 4,015,939 A | 4/1977 | Lewin et al. | |
| 4,110,470 A | 8/1978 | Kummer | |
| 4,115,537 A | 9/1978 | Driscoll et al. | |
| 4,288,546 A | 9/1981 | Narasimhan et al. | |
| 4,344,934 A | 8/1982 | Martin et al. | |
| 4,369,172 A | 1/1983 | Schor et al. | |
| 4,479,947 A | 10/1984 | Christensen et al. | |
| 4,539,198 A | 9/1985 | Powell et al. | |

(Continued)

FOREIGN PATENT DOCUMENTS

DE    4318577    12/1994

(Continued)

OTHER PUBLICATIONS

A *copy* of the International Search Report dated Sep. 12, 2002.

(Continued)

*Primary Examiner*—Humera N. Sheikh
(74) *Attorney, Agent, or Firm*—Kramer Levin Naftalis & Frankel LLP.; Jessica Jamieson

(57) ABSTRACT

A pharmaceutical composition with β-sheet microcrystalline cellulose with improved potency life and methods of preparation therefor. Improved thyroid hormone pharmaceutical compositions comprising 50 weight % or more of β-sheet microcrystalline cellulose.

24 Claims, 2 Drawing Sheets

Cylindrical Dosage

Oblong Dosage

Raised Violin Dosage

U.S. PATENT DOCUMENTS

| | | | |
|---|---|---|---|
| 4,585,652 A | 4/1986 | Miller et al. |
| 4,587,258 A | 5/1986 | Gold et al. |
| 4,615,697 A | 10/1986 | Robinson et al. |
| 4,654,331 A | 3/1987 | Christensen et al. |
| 4,666,703 A | 5/1987 | Kopf et al. |
| 4,690,824 A | 9/1987 | Powell et al. |
| 4,705,692 A | 11/1987 | Tanaka et al. |
| 4,795,436 A | 1/1989 | Robinson et al. |
| 4,795,644 A | 1/1989 | Zentner et al. |
| 4,814,183 A | 3/1989 | Zentner et al. |
| 4,818,531 A | 4/1989 | Anderson et al. |
| 4,851,228 A | 7/1989 | Zentner et al. |
| 4,877,774 A | 10/1989 | Pitha et al. |
| 4,960,690 A | 10/1990 | Ellis et al. |
| 4,973,469 A | 11/1990 | Mulligan et al. |
| 4,980,358 A | 12/1990 | Smith et al. |
| 4,983,392 A | 1/1991 | Robinson et al. |
| 5,001,115 A | 3/1991 | Sloan et al. |
| 5,061,722 A | 10/1991 | Teetz et al. |
| 5,064,823 A | 11/1991 | Lee et al. |
| 5,073,379 A | 12/1991 | Klimesch et al. |
| 5,073,555 A | 12/1991 | Smith et al. |
| 5,099,001 A | 3/1992 | Scarano et al. |
| 5,158,978 A | 10/1992 | Rubin et al. |
| 5,176,953 A | 1/1993 | Jacoby et al. |
| 5,225,196 A | 7/1993 | Robinson et al. |
| 5,225,204 A * | 7/1993 | Chen et al. |
| 5,244,786 A | 9/1993 | Picone et al. |
| 5,310,912 A | 5/1994 | Neumeyer et al. |
| 5,317,035 A | 5/1994 | Jacoby et al. |
| 5,324,522 A | 6/1994 | Krenning et al. |
| 5,412,005 A | 5/1995 | Bastioli et al. |
| 5,439,666 A | 8/1995 | Neumeyer et al. |
| 5,449,522 A | 9/1995 | Hill et al. |
| 5,461,140 A | 10/1995 | Heller et al. |
| 5,574,150 A * | 11/1996 | Yaginuma et al. |
| 5,594,070 A | 1/1997 | Jacoby et al. |
| 5,607,691 A | 3/1997 | Hale et al. |
| 5,618,338 A | 4/1997 | Kurabayashi et al. |
| 5,624,612 A | 4/1997 | Sewall et al. |
| 5,635,209 A | 6/1997 | Groenewoud et al. |
| 5,648,096 A | 7/1997 | Gander et al. |
| 5,656,286 A | 8/1997 | Miranda et al. |
| 5,670,380 A | 9/1997 | Wu et al. |
| 5,686,094 A | 11/1997 | Acharya et al. |
| 5,698,179 A | 12/1997 | Neumeyer et al. |
| 5,718,969 A | 2/1998 | Sewall et al. |
| 5,728,810 A | 3/1998 | Lewis et al. |
| 5,738,984 A | 4/1998 | Shoseyov et al. |
| 5,750,089 A | 5/1998 | Neumeyer et al. |
| 5,753,254 A * | 5/1998 | Khan et al. |
| 5,767,227 A | 6/1998 | Latham et al. |
| 5,784,992 A | 7/1998 | Petitte et al. |
| 5,800,836 A | 9/1998 | Morella et al. |
| 5,811,547 A | 9/1998 | Nakamichi et al. |
| 5,856,359 A | 1/1999 | Fischer et al. |
| 5,888,774 A | 3/1999 | Delcuve et al. |
| 5,897,910 A | 4/1999 | Rosenberg et al. |
| 5,910,569 A | 6/1999 | Latham et al. |
| 5,916,910 A | 6/1999 | Lai et al. |
| 5,939,099 A | 8/1999 | Grabowski et al. |
| 5,945,127 A | 8/1999 | Breitenbach et al. |
| 5,952,451 A | 9/1999 | Zhao et al. |
| 5,955,105 A * | 9/1999 | Mitra et al. |
| 5,958,453 A | 9/1999 | Ohno et al. |
| 5,958,979 A * | 9/1999 | Lahr et al. |
| 5,985,607 A | 11/1999 | Delcuve et al. |
| 5,989,894 A | 11/1999 | Lewis et al. |
| 6,001,391 A | 12/1999 | Zeidler et al. |
| 6,008,318 A | 12/1999 | Zhao et al. |
| 6,009,690 A | 1/2000 | Rosenberg et al. |
| 6,024,976 A | 2/2000 | Miranda et al. |
| 6,030,613 A | 2/2000 | Blumberg et al. |
| 6,046,177 A | 4/2000 | Stella et al. |
| 6,051,253 A | 4/2000 | Zettler et al. |
| 6,056,975 A | 5/2000 | Mitra et al. |
| 6,080,383 A | 6/2000 | Rose et al. |
| 6,080,426 A | 6/2000 | Amey et al. |
| 6,110,909 A | 8/2000 | Yukimasa et al. |
| 6,117,911 A | 9/2000 | Grainger et al. |
| 6,120,802 A | 9/2000 | Breitenbach et al. |
| 6,132,659 A | 10/2000 | Rosenberg et al. |
| 6,143,717 A | 11/2000 | Hill et al. |
| 6,150,424 A | 11/2000 | Breitenbach et al. |
| 6,153,223 A | 11/2000 | Apelian et al. |
| 6,183,596 B1 | 2/2001 | Matsuda et al. |
| 6,187,342 B1 | 2/2001 | Zeidler et al. |
| 6,190,591 B1 | 2/2001 | van Lengerich et al. |
| 6,190,696 B1 * | 2/2001 | Groenewoud |
| 6,200,958 B1 | 3/2001 | Odaka et al. |
| 6,211,402 B1 | 4/2001 | Kleiner |
| 6,214,163 B1 | 4/2001 | Matsuda et al. |
| 6,221,383 B1 | 4/2001 | Miranda et al. |
| 6,221,402 B1 | 4/2001 | Itoh et al. |
| 6,245,350 B1 | 6/2001 | Amey et al. |
| 6,248,357 B1 | 6/2001 | Ohno et al. |
| 6,261,537 B1 | 7/2001 | Klaveness et al. |
| 6,268,197 B1 | 7/2001 | Schulein et al. |
| 6,284,271 B1 | 9/2001 | Lundberg et al. |
| 6,284,803 B1 | 9/2001 | Kothrade et al. |
| 6,290,990 B1 | 9/2001 | Grabowski et al. |
| 6,299,904 B1 | 10/2001 | Shimizu et al. |
| 6,323,236 B1 | 11/2001 | McElroy |
| 6,328,979 B1 | 12/2001 | Yamashita et al. |
| 6,328,994 B1 | 12/2001 | Shimizu et al. |
| 6,331,316 B1 | 12/2001 | Ullah et al. |
| 6,340,471 B1 | 1/2002 | Kershman et al. |
| 6,350,398 B1 | 2/2002 | Breitenbach et al. |
| 6,372,255 B1 | 4/2002 | Saslawski et al. |
| 6,383,471 B1 | 5/2002 | Chen et al. |
| 6,395,300 B1 | 5/2002 | Straub et al. |
| 6,399,101 B1 * | 6/2002 | Frontanes et al. |
| 6,403,675 B1 | 6/2002 | Dang et al. |
| 6,406,297 B1 | 6/2002 | Raymond et al. |
| 6,410,587 B1 | 6/2002 | Grainger et al. |
| 6,414,126 B1 | 7/2002 | Ellsworth et al. |
| 6,423,256 B1 | 7/2002 | Kothrade et al. |
| 6,458,842 B1 | 10/2002 | Dickinson et al. |
| 6,468,503 B1 | 10/2002 | Rose et al. |
| 6,471,734 B1 | 10/2002 | Yeckley et al. |
| 6,485,726 B1 | 11/2002 | Blumberg et al. |
| 6,488,961 B1 | 12/2002 | Robinson et al. |
| 6,491,946 B1 * | 12/2002 | Schreder et al. |
| 6,495,740 B1 | 12/2002 | Arioli et al. |
| 6,499,984 B1 | 12/2002 | Ghebre-Sellassie et al. |
| 6,500,658 B1 | 12/2002 | Wu et al. |
| 6,555,581 B1 | 4/2003 | Franz et al. |

FOREIGN PATENT DOCUMENTS

| | | |
|---|---|---|
| DE | 19541128 | 10/1995 |
| DE | 19801625 A1 | 7/1999 |
| DE | 19830246 | 1/2000 |
| EP | 0202051 | 11/1986 |
| EP | 248548 | 12/1987 |
| EP | 255404 | 2/1988 |
| EP | 256878 | 2/1988 |
| EP | 259157 | 3/1988 |
| EP | 268912 | 6/1988 |
| EP | 271204 | 6/1988 |
| EP | 278908 | 8/1988 |
| EP | 287189 | 10/1988 |
| EP | 295742 | 12/1988 |
| EP | 297290 | 1/1989 |

| | | | | | |
|---|---|---|---|---|---|
| EP | 299533 | 1/1989 | EP | 682113 | 11/1995 |
| EP | 300676 | 1/1989 | EP | 687675 | 12/1995 |
| EP | 304156 | 2/1989 | EP | 610334 | 1/1996 |
| EP | 307152 | 3/1989 | EP | 684511 | 1/1996 |
| EP | 307970 | 3/1989 | EP | 697819 | 2/1996 |
| EP | 297292 | 4/1989 | EP | 705607 | 4/1996 |
| EP | 310179 | 4/1989 | EP | 707848 | 4/1996 |
| EP | 312157 | 4/1989 | EP | 0839526 | 6/1996 |
| EP | 313515 | 4/1989 | EP | 381719 | 9/1996 |
| EP | 317070 | 5/1989 | EP | 471794 | 10/1996 |
| EP | 327918 | 8/1989 | EP | 737742 | 10/1996 |
| EP | 328106 | 8/1989 | EP | 741188 | 11/1996 |
| EP | 354322 | 2/1990 | EP | 742228 | 11/1996 |
| EP | 360006 | 3/1990 | EP | 754464 | 1/1997 |
| EP | 360258 | 3/1990 | EP | 759441 | 2/1997 |
| EP | 367463 | 5/1990 | EP | 482080 | 3/1997 |
| EP | 371683 | 6/1990 | EP | 620809 | 3/1997 |
| EP | 384522 | 8/1990 | EP | 761219 | 3/1997 |
| EP | 396282 | 11/1990 | EP | 761220 | 3/1997 |
| EP | 410411 | 1/1991 | EP | 769300 | 4/1997 |
| EP | 234708 | 2/1991 | EP | 770606 | 5/1997 |
| EP | 417721 | 3/1991 | EP | 696283 | 9/1997 |
| EP | 417840 | 3/1991 | EP | 796849 | 9/1997 |
| EP | 418596 | 3/1991 | EP | 532533 | 10/1997 |
| EP | 422699 | 4/1991 | EP | 812195 | 12/1997 |
| EP | 212603 | 6/1991 | EP | 482071 | 1/1998 |
| EP | 430190 | 6/1991 | EP | 823437 | 2/1998 |
| EP | 433043 | 6/1991 | EP | 834507 | 4/1998 |
| EP | 437367 | 7/1991 | EP | 839526 | 5/1998 |
| EP | 212599 | 10/1991 | EP | 578728 | 7/1998 |
| EP | 452862 | 10/1991 | EP | 862562 | 9/1998 |
| EP | 455042 | 11/1991 | EP | 870826 | 10/1998 |
| EP | 459226 | 12/1991 | EP | 890360 | 1/1999 |
| EP | 137280 | 3/1992 | EP | 895988 | 2/1999 |
| EP | 201071 | 3/1992 | EP | 773951 | 3/1999 |
| EP | 475148 | 3/1992 | EP | 905129 | 3/1999 |
| EP | 476645 | 3/1992 | EP | 625164 | 4/1999 |
| EP | 476646 | 3/1992 | EP | 907364 | 4/1999 |
| EP | 476658 | 3/1992 | EP | 753003 | 6/1999 |
| EP | 477286 | 4/1992 | EP | 919620 | 6/1999 |
| EP | 477827 | 4/1992 | EP | 921194 | 6/1999 |
| EP | 484785 | 5/1992 | EP | 945443 | 9/1999 |
| EP | 487774 | 6/1992 | EP | 952148 | 10/1999 |
| EP | 506211 | 9/1992 | EP | 654038 | 11/1999 |
| EP | 510662 | 10/1992 | EP | 957091 | 11/1999 |
| EP | 518587 | 12/1992 | EP | 962466 | 12/1999 |
| EP | 1 161 946 A2 | 3/1993 | EP | 962530 | 12/1999 |
| EP | 271974 | 3/1993 | EP | 817792 | 3/2000 |
| EP | 532611 | 3/1993 | EP | 984063 | 3/2000 |
| EP | 239306 | 6/1993 | EP | 990703 | 4/2000 |
| EP | 0 550 108 A1 | 7/1993 | EP | 995759 | 4/2000 |
| EP | 556395 | 8/1993 | EP | 673383 | 5/2000 |
| EP | 559785 | 9/1993 | EP | 996424 | 5/2000 |
| EP | 567541 | 11/1993 | EP | 1004572 | 5/2000 |
| EP | 574185 | 12/1993 | EP | 1004578 | 5/2000 |
| EP | 577243 | 1/1994 | EP | 1004580 | 5/2000 |
| EP | 601486 | 6/1994 | EP | 1004581 | 5/2000 |
| EP | 604983 | 7/1994 | EP | 1006187 | 6/2000 |
| EP | 605729 | 7/1994 | EP | 1022286 | 7/2000 |
| EP | 301064 | 8/1994 | EP | 1022336 | 7/2000 |
| EP | 619371 | 10/1994 | EP | 759937 | 8/2000 |
| EP | 620278 | 10/1994 | EP | 1012151 | 8/2000 |
| EP | 623343 | 11/1994 | EP | 1029897 | 8/2000 |
| EP | 624646 | 11/1994 | EP | 938557 | 9/2000 |
| EP | 624647 | 11/1994 | EP | 1033364 | 9/2000 |
| EP | 624648 | 11/1994 | EP | 1041072 | 10/2000 |
| EP | 624649 | 11/1994 | EP | 1043333 | 10/2000 |
| EP | 628631 | 12/1994 | EP | 1046896 | 10/2000 |
| EP | 653935 | 5/1995 | EP | 1051082 | 11/2000 |
| EP | 510091 | 6/1995 | EP | 1074622 | 2/2001 |
| EP | 659883 | 6/1995 | EP | 1077259 | 2/2001 |
| EP | 210581 | 7/1995 | EP | 1077681 | 2/2001 |
| EP | 669831 | 9/1995 | EP | 1086947 | 3/2001 |

| | | |
|---|---|---|
| EP | 797437 | 4/2001 |
| EP | 1088550 | 4/2001 |
| EP | 1088819 | 4/2001 |
| EP | 1090992 | 4/2001 |
| EP | 1097928 | 5/2001 |
| EP | 1104758 | 6/2001 |
| EP | 1104759 | 6/2001 |
| EP | 1104760 | 6/2001 |
| EP | 1104771 | 6/2001 |
| EP | 1106612 | 6/2001 |
| EP | 731808 | 7/2001 |
| EP | 862562 | 7/2001 |
| EP | 1113008 | 7/2001 |
| EP | 1113020 | 7/2001 |
| EP | 1114826 | 7/2001 |
| EP | 1118858 | 7/2001 |
| EP | 1127882 | 8/2001 |
| EP | 538297 | 9/2001 |
| EP | 800505 | 9/2001 |
| EP | 1132392 | 9/2001 |
| EP | 1134215 | 9/2001 |
| EP | 1138680 | 10/2001 |
| EP | 1142889 | 10/2001 |
| EP | 1145711 | 10/2001 |
| EP | 1146051 | 10/2001 |
| EP | 1147879 | 10/2001 |
| EP | 1148054 | 10/2001 |
| EP | 715653 | 11/2001 |
| EP | 836475 | 11/2001 |
| EP | 1153940 | 11/2001 |
| EP | 1161941 | 12/2001 |
| EP | 1167376 | 1/2002 |
| EP | 1167386 | 1/2002 |
| EP | 1178115 | 2/2002 |
| EP | 1188769 | 3/2002 |
| EP | 1191025 | 3/2002 |
| EP | 653935 | 5/2002 |
| EP | 1203580 | 5/2002 |
| EP | 814831 | 6/2002 |
| EP | 1032571 | 6/2002 |
| EP | 1225182 | 7/2002 |
| EP | 1227103 | 7/2002 |
| EP | 806964 | 8/2002 |
| EP | 724587 | 9/2002 |
| EP | 972020 | 9/2002 |
| EP | 1041972 | 9/2002 |
| EP | 1236739 | 9/2002 |
| EP | 1236797 | 9/2002 |
| EP | 1238964 | 9/2002 |
| EP | 1241261 | 9/2002 |
| EP | 706521 | 10/2002 |
| EP | 1077681 | 10/2002 |
| EP | 1149842 | 10/2002 |
| EP | 1245567 | 10/2002 |
| EP | 1247456 | 10/2002 |
| EP | 1247810 | 10/2002 |
| EP | 1251137 | 10/2002 |
| EP | 1258495 | 11/2002 |
| EP | 1258496 | 11/2002 |
| EP | 917534 | 12/2002 |
| EP | 1161940 | 12/2002 |
| EP | 1262177 | 12/2002 |
| EP | 1262180 | 12/2002 |
| EP | 1264843 | 12/2002 |
| GB | 180574 | 6/1921 |
| WO | WO 94/03160 | 2/1994 |
| WO | WO 95/12604 | 5/1995 |
| WO | WO 95/12605 | 5/1995 |
| WO | WO 95/14033 | 5/1995 |
| WO | WO 95/20953 | 8/1995 |
| WO | WO 95/20954 | 8/1995 |
| WO | WO 99/59551 | 6/1996 |
| WO | WO 97/10224 | 3/1997 |
| WO | WO 97/17951 | 5/1997 |
| WO | WO 00/06126 | 7/1998 |
| WO | WO 98/46270 | 10/1998 |
| WO | WO 98/46588 | 10/1998 |
| WO | WO 98/47002 | 10/1998 |
| WO | WO98/53798 | 12/1998 |
| WO | WO 99/04813 | 2/1999 |
| WO | WO 99/29327 | 6/1999 |
| WO | WO 99/30690 | 6/1999 |
| WO | WO 99/33448 | 7/1999 |
| WO | WO 99/59544 | 11/1999 |
| WO | WO9959551 | 11/1999 |
| WO | WO 99/62499 | 12/1999 |
| WO | WO 99/62969 | 12/1999 |
| WO | WO 99/63969 | 12/1999 |
| WO | WO 00/02586 | 1/2000 |
| WO | WO 02/096401 A1 | 2/2000 |
| WO | WO 00/50020 | 8/2000 |
| WO | WO 01/49272 A2 | 7/2001 |
| WO | WO 01/74448 A1 | 10/2001 |
| WO | WO2001074448 | 10/2001 |
| WO | WO 01/80822 A2 | 11/2001 |
| WO | WO 01/83093 A1 | 11/2001 |
| WO | WO 01/89679 A2 | 11/2001 |
| WO | WO 01/98282 A1 | 12/2001 |
| WO | WO 02/03914 A2 | 1/2002 |
| WO | WO 02/09671 A2 | 2/2002 |
| WO | WO 02/26262 A2 | 4/2002 |
| WO | WO 02/28364 A2 | 4/2002 |
| WO | WO 02/28365 A2 | 4/2002 |
| WO | WO2002028364 | 4/2002 |
| WO | WO2002028365 | 4/2002 |
| WO | WO 02/45693 A1 | 6/2002 |
| WO | WO 02/056861 A2 | 7/2002 |
| WO | WO2002056861 | 7/2002 |
| WO | WO 01/059106 A1 | 8/2002 |
| WO | WO 01/064093 A2 | 8/2002 |
| WO | WO 064093 A2 | 8/2002 |
| WO | WO 02/067854 A2 | 9/2002 |
| WO | WO 02/069977 A1 | 9/2002 |
| WO | WO 02/096401 A1 | 12/2002 |
| WO | WO 03/013441 | 2/2003 |
| WO | WO 03/028624 | 4/2003 |
| WO | WO 03/061557 | 7/2003 |
| WO | PCT/US03/25170 | 8/2003 |
| WO | WO 03/070217 | 8/2003 |

OTHER PUBLICATIONS

A. Faure et al. *J. Pharm. Pharmacol.* 50:(12) 1431-1432 (1998).

K. P. R. Chowdary and T. Manjula: Effect of Selected Binders and Disintegrants on the dissolution Rate of Nimesulide from Tablets Indian J. Pharm. Sci. 62: (3) 224-228 (2000).

A. K. Dwivedi et al. Development of Stable Formulation of Picroliv a new Hepatoprotective Agent Indian *Journal of Pharmaceutical Science.* 57: (2) 88-90 (Mar.-Apr. 1995).

A. E. Beezer et al. Letter to the Editor, Comments on Serger et al.'s (1998 1999) calorimetric stability studies *International Journal of Pharmaceutics* 207/1-2: 117-118 (Oct. 10, 2000).

G. Bardini et al. Letters Effect of different Pharmacological formulations of Gliclazide on Postprandial Hyperglycaemia *Diabetic Medicine* 15: (8) 706-708 (1998).

R. Ek et al. Letter to the Editor Microcrystalline Cellulose as a Sponge as an Alternative Concept to the Crystallite-Gel Model for Extrusion and Spheronization *Pharamceutical Research* 15: (4) 509-512 (1998).

R. S. Chapman and J. G. Ratcliffe Brief technical note Covalent linkage of antisera to microparticulate cellulose using 11'-carbontyldiimidazole: a rapid practical method with potential use in solid-phase immunoassay *Clinica Chimica Acta* 118: (1) 129-134 (1982).

J. Seth et al. Simple Solid-Phase Radioimmunoassays for Total Tri-iodothyronine and Thyroxine in Serum and their clinical evaluation *Clinica Chimica Acta* 68: (3) 291-301 (May 3, 1976).

M. Nakamura and Sachiya Ohtaki Formation and Reduction of Ascorbate Radicals by Hog Thyuroid Microsomes *Archives of Biochemistry and Biophysics* 305: (1) 84-90 (Aug. 15, 1993).

R. S. Rapaka et al. Facile hydrolytic cleavage of NO-diheptafluorobutyryl derivatives of thyroidal amino acids *Journal of Chromatography* 236: 496-498 (1982).

Novelty Computer Search for Levothyroxine and Microcrystalline Cellulose pp. 4-129 (2002).

P.J.J. De Meijer. Analysis of thyroid and Thyroxin by Means of High Performance Liquid Chromatography Pharmaceutisch Weekblad 116: 1085-1089 (1981).

Ceolus™ Microcrystalline Cellulose NF Ph. Eur. JP for Smaller Tablets FMC pp. 1-6 (Oct. 1, 1997).

Avicel PH Microcrystalline Cellulose NF Ph. Eur. JP B A World of Difference FMC BioPolymer pp. 1-11 (Oct. 1, 1998).

Food and Drug Administration Notice Regarding Levothyroxine Sodium Deartment of Health and Human Science FDA Federal Register 62(157):1-12 (Aug. 14, 1997).

Jerome Stevens Pharmaceuticals Inc. Petition to FD pp. 1-129 (Mar. 28, 2002) (File Copy).

Surface Profile Parameters Surface Meterology Guide—Profile Parameters pp. 1-23 (Jan. 30, 2001).

Surface Profile Parameteters Surface Meterology Guid—Profile Parameters pp. 1-12 (130/01).

Electropolishing pp. 1-3 (Jan. 30, 2001).

Thyroid Hormone Synthetic Class 72120 Source: NDC Health's PhAst Combined d?mail Order + Non Retail for the years 2001-2002 pp. 1-6 (2002).

Obae et al.: International Journal of Pharmaceutics 182(199): 155-164 (1999).

Ceolus KG-801 Certificate of Analysis Asahi Chemical Co. LTD 1 page (Jan. 7, 1999).

Ceolus KG-801 Certificate of Analysis Asahi Chemical Co. LTD 1 page (Jun. 24, 2002).

Ceolus KG-802 Certificate of Analysis Asahi Kasei Corp. 1 page (Jun. 19, 2001).

Ceolus KG-802 Certificate of Analysis Asahi Kasei Corp. 1 page (Nov. 26, 2002).

Avicel PH-101 Certificate of Analysis FMC BioPolymer 1 page (Aug. 21, 2001).

Avicel PH-102 Certificate of Analysis FMC BioPolymer 1 page (Aug. 18, 2002).

Ceolus™ Microcrystalline Cellulose NF Ph. Eur. JP 6 pages (CEOL-Oct. 1997).

Asashi Chemical Japan's leading supplier of pharmaceutical excipients 10 pages (Nov. 2000).

Letter to FD from Asahi Chemical Industry Co. Ltd. Drug Master File 13834 for Ceolus KG™ 1 page Feb. 19, 2000).

S. Stofer et al.: JAMA 251(5):635-636 (1984).

M. Chong: Pharmaceutical Research 9(1):131-137 (1992).

J. Brower et al. J. Pharmaceutical Sciences 73(9): 1315-1317 (1984).

S. Richheimer et al.: J. Pharmaceutical Sciences 72(11):1351-1353 (1983).

V. Das Gupta et al.: J. Clinical Pharmacy and Therapeutics 15:331-336 (1990).

M. Andre et al.: J. Chromatography A 725:287-294 (1996).

Federal Register 65(157):43535-43538 (Aug. 14, 1997).

Combined Retail/Mail Order + Non-Retail NDC Health's PhASt Class 72120 Thyroid Hormone Synthetic Order + Non Retail.

International Journal of Pharmaceutics vol. 182 No. 199 p. 155.

The complete specification including brand name and product number for the B- microcrystalline cellulose which was described in the patent application.

Updated court docket for King Pharmaceuticals, Inc., & Jones Pharma, Inc. v. KV Pharmaceutical Co., C.A. No. 03-cv-786 (D.Del.).

Updated court docket for King Pharmaceuticals, Inc., & Jones Pharma, Inc. v. Mylan Pharmaceuticals, Inc., C.A. No. 03-cv-153 (N.D.W.V.).

Answer and Counterclaim (of KV Pharmaceuticals, Co.).

Answer, Affirmative Defenses and Counterclaims for Defendant Mylan Pharmaceuticals, Inc.

* cited by examiner

Cylindrical Dosage

Oblong Dosage

Raised Violin Dosage

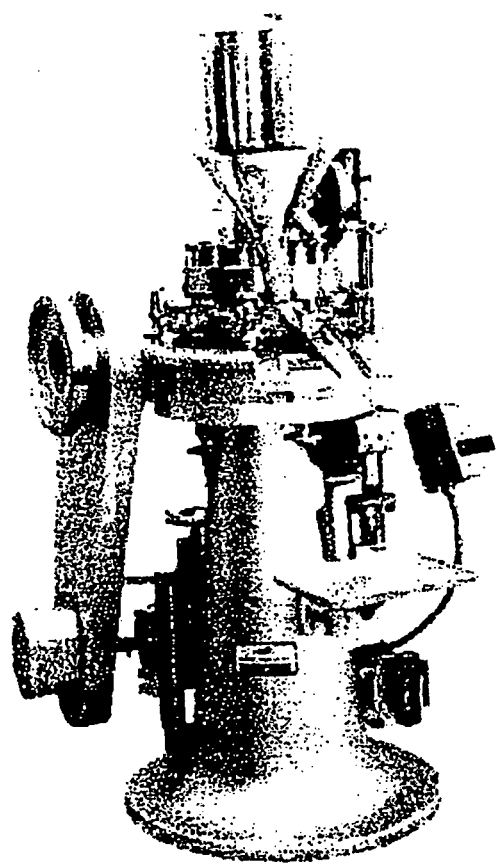
Figure 2 – Manesty Tableting Machine
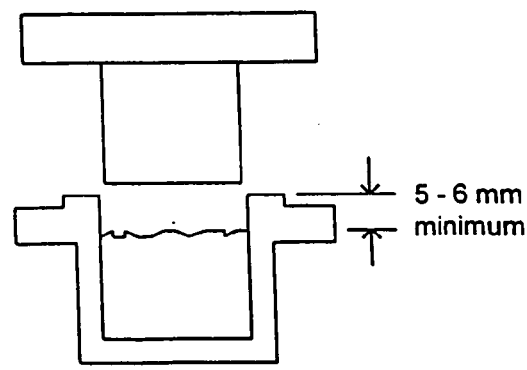
Figure 3 – Extra Deep Tableting Dies

STABILIZED PHARMACEUTICAL AND THYROID HORMONE COMPOSITIONS AND METHOD OF PREPARATION

This application claims benefit of provisional Application No. 60/269,009 filed Feb. 15, 2001

BACKGROUND

The present invention relates to solid pharmaceutical compositions and the method of preparing the same. More specifically, the present invention relates to the preparation of stabilized pharmaceutical compositions, using pharmaceutically active ingredients such as levothyroxine sodium and liothyronine sodium (thyroid hormone drugs), in a solid dosage form. Said stabilized hormone compositions are prepared by blending the active moiety and β-sheet form of microcrystalline cellulose and compressing to the desired solid dosage forms.

Thyroid hormone preparations of levothyroxine sodium and liothyronine sodium are pharmaceutical preparations useful in the treatment of hypothyroidism and thyroid hormone replacement therapy in mammals, for example, humans and dogs.

Thyroid hormone preparations are used to treat reduced or absent thyroid function of any etiology, including human or animal ailments such as myxedema, cretinism and obesity.

Hypothyroidism is a common condition. It has been reported in the United States Federal Register that Hypothyroidism has a prevalence of 0.5 percent to 1.3 percent in adults. In people over 60, the prevalence of primary hypothyroidism increases to 2.7 percent in men and 7.1 percent in women. Because congenital hypothyroidism may result in irreversible mental retardation, which can be avoided with early diagnosis and treatment, newborn screening for this disorder is mandatory in North America, Europe, and Japan.

Thyroid hormone replacement therapy can be a chronic, lifetime endeavor. The dosage is established for each patient individually. Generally, the initial dose is small. The amount is increased gradually until clinical evaluation and laboratory tests indicate that an optimal response has been achieved. The dose required to maintain this response is then continued. The age and general physical condition of the patient and the severity and duration of the hypothyroid symptoms determine the initial dosage and the rate at which the dosage may be increased to the eventual maintenance level. It has been reported that the dosage increase should be very gradual in patients with myxedema or cardiovascular disease to prevent precipitation of angina, myocardial infarction, or stroke.

It is important that thyroid hormone treatment have the correct dosage. Both under treatment and over treatment can have deleterious health impacts. In the case of under treatment, a sub-optimal response and hypothyroidism could result, under treatment has also been reported to be a potential factor in decreased cardiac contractility and increased risk of coronary artery disease. Conversely, over treatment may result in toxic manifestations of hyperthyroidism such as cardiac pain, palpitations, or cardiac arrhythmias. In patients with coronary heart disease, even a small increase in the dose of levothyroxine sodium may be hazardous in a particular.

Hyperthyroidism is a known risk factor for osteoporosis. Several studies suggest that subclinical hyperthyroidism in premenopausal women receiving thyroid hormone drugs for replacement or suppressive therapy is associated with bone loss. To minimize the risk of osteoporosis it is preferable that the dose be kept to the lowest effective dose.

Because the risks associated with over treatment or under treatment with levothyroxine sodium, there is a need for thyroid hormone products that are consistent in potency and bioavailability. Such consistency is best accomplished by manufacturing techniques that maintain consistent amounts of the active moiety during tablet manufacture.

Thyroid hormone drugs are natural or synthetic preparations containing tetraiodothyronine ($T_4$, levothyroxine) sodium or triiodothyronine ($T_3$, liothyronine) sodium or both. $T_4$ and $T_3$ are produced in the human thyroid gland by the iodination and coupling of the amino acid tyroisine. $T_4$ contains four iodine atoms and is formed by the coupling of two molecules of diiodotyrosine (DIT). $T_3$ contains three atoms of iodine and is formed by the coupling of one molecule of DIT with one molecule of moniodotyrosine (MIT). Both hormones are stored in the thyroid colloid as thyroglobulin. Thyroid hormone preparations belong to two categories: (1) natural hormonal preparations derived from animal thyroid, and (2) synthetic preparations. Natural preparations include desiccated thyroid and thyroglobulin.

Desiccated thyroid is derived from domesticated animals that are used for food by man (either beef or hog thyroid), and thyroglobulin is derived from thyroid glands of the hog. The United States Pharamcopoeia (USP) has standardized the total iodine content of natural preparations. Thyroid USP contains not less than (NLT) 0.17 percent and not more than (NMT) 0.23 percent iodine, and thyroglobulin contains not less than (NLT) 0.7 percent of organically bound iodine. Iodine content is only an indirect indicator of true hormonal biologic activity.

Synthetic forms for both $T_4$ and $T_3$ thyroid hormone are available from a number of producers. For example, liothyronine sodium ($T_3$) tablets are available from Jones Pharma, St. Louis, Mo. under the trademark Cytomel (now King Pharmaceuticals, Inc.) Levothyroxine sodium ($T_4$) is available under the tradename Levoxyl from Jones Pharma (now King Pharmaceuticals, Inc.), under the tradename Synthroid from Knoll Pharmaceutical, Mt. Olive, N.J., and under the tradename Unithroid from Jerome Stevens Pharmaceuticals, Bohemia, N.Y. In addition a veterinarian preparation of levothyroxine sodium is available under the tradename Soloxine from Jones Pharma, St. Louis, Mo.

It is well known that the stability of thyroid hormone drugs are quire poor. They are hygroscopic and they degrade in the presence of moisture or light, and under conditions of high temperature. The instability is especially notable in the presence of pharmaceutical excipients, such as carbohydrates, including lactose, sucrose, dextrose and starch, as well as certain dyes.

It is desirable, therefore, to prepare a stabilized dosage of levothyroxine and liothyronine, which will have a longer shelf life that can be used in the treatment of human or animal thyroid hormone deficiency, U.S. Pat. No. 5,225,204 (the '204 patent) is directed to improving the stability of levothyroxine sodium. In one embodiment disclosed by '204, stabilized levothyroxine sodium was prepared in a dry state by mixing levothyroxine sodium with a cellulose tableting agent using geometric dilution and subsequently combining this mixture with the same or a second cellulose tableting agent, such as microcrystalline cellulose. Other tableting aids or excipients can be used in this formulation. This '204 patent is incorporated by reference herein in its entirety.

The microcrystalline cellulose disclosed in '204 is AVICEL 101, 102, 103, 105, trademarks of FMC Company of Newark, Del., and Microcrystalline Cellulose NF, or EMCOCEL, a trademark owned by Penwest Pharmaceuticals of Patterson, N.Y. These microcrystalline cellulose products are prepared by re-slurryng the cellulose and spray-draying the product. This produces an α-helix spherical microcrystalline cellulose product.

U.S. Pat. Nos. 5,955,015 and 6,056,975 (the continuation of '105) disclose a stabilized pharmaceutical preparation of levothyroxine and microcrystalline cellulose, along with other excipients. The microcrystalline cellulose products used by '105 and '975 were also the α-form Avicel microcrystalline cellulose products. U.S. Pat. Nos. 5,955,105 and 6,056,975 are incorporated by reference herein, in their entirety.

The microcrystalline cellulose product of the present invention is prepared by making a wet cake and drying it with a drum dryer, then passing the dried product through a screen or mill for sizing, which produces a β-sheet form microcrystalline cellulose which has a flat needle shape. Such β-sheet microcrystalline cellulose is marketed under the trademark CEOLUS KG801 by FMC Company of Newark, Del. Said Ceolus product has different morphology, and therefore different performance characteristics, than those of the Avicel product, and is suitable for preparing the present stabilized pharmaceutical product.

The β-sheet microcrystalline cellulose of the present invention is disclosed in the U.S. Pat. No. 5,574,150, which is hereby incorporated by reference. Further disclosure relating to β-sheet microcrystalline cellulose is found in *International Journal of Pharmaceutics* 182 (199) 155 which is hereby incorporated by reference.

The Ceolus product (β-sheet microcrystalline cellulose) is disclosed by FMC in its product bulletin dated October 1997 as being suitable for "smaller size tablets" and "exceptional drug carrying capacity." Such Ceolus product was to provide superior compressibility and drug loading capacity that still exhibited effective flowability. The examples given in the bulleting are of vitamin C combined with Ceolus microcrystalline cellulose at levels of from 30 to 45 weight % Ceolus product in the form of a tablet. At higher levels of Ceolus product concentration, flow problems were encountered in the process of compressing tablets, and the Ceolus product was deemed unsuitable for compressions at higher concentrations than about 45 weight %.

None of the references listed above disclose the present invention of a stabilized pharmaceutical composition comprising a pharmaceutically active ingredient, such as levothyroxine, and at least about 50 weight % the β-sheet form of microcrystalline cellulose.

SUMMARY OF THE INVENTION

The present invention relates to a stabilized pharmaceutical composition comprising a pharmaceutically active ingredient, such as levothyroxine, and the β-sheet form of microcrystalline cellulose, in the form of a solid dosage. More specifically, the present invention relates to a stabilized pharmaceutical composition comprising a pharmaceutically active ingredient, such as levothyroxine sodium and/or liothyronine sodium, at least about 50 weight % of the dosage weight composed of the β-sheet form of microcrystalline cellulose, and, optionally, additional excipients, in a solid dosage form.

Further, the present invention relates to a method of preparing an oral dosage form of a pharmaceutically active ingredient comprising dry blending the pharmaceutically active ingredient and at least about 50 weight % of the β-sheet form of microcrystalline cellulose, and compressing the blend to form a solid dosage.

BRIEF DESCRIPTION OF DRAWINGS

FIG. 2 illustrates a Manesty tableting machine;
FIG. 3 illustrates a tableting die pair;
Exhibit A indicates testing of tableting machines.
Exhibit B illustrates stability testing of various solid dosage formulations.

DETAILED DESCRIPTION

Figure 1:
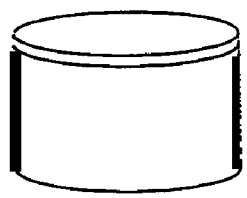
FIG. 1 illustrates various solid dosage forms such as cylindrical tablets and raised violin shaped tablets.
Figure 1:
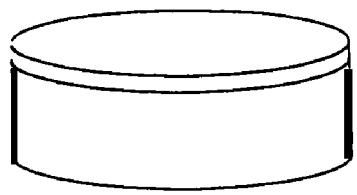
Figure 1:
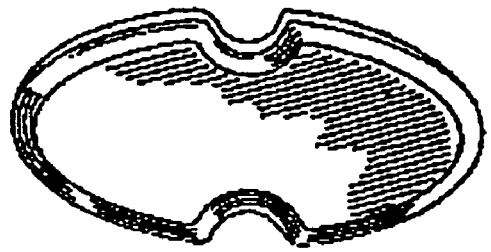

The present invention is a pharmaceutical product that is in the form of a solid dosage, such as a sublingual lozenge, buccal tablet, oral lozenge, suppository or a compressed tablet. The pharmaceutically active ingredient is dry mixed with the β-sheet form of the microcrystalline cellulose, optionally with additional excipients, and formed into a suitable solid dosage.

The present invention can be prepared as a direct compression formula, dry granulation formula, or as a wet granulation formula, with or without preblending of the drug, although preferably with preblending.

The pharmaceutically active ingredient can be any type of medication which acts locally in the mouth or systematically, which is the case of the latter, can be administered orally to transmit the active medicament into the gastrointestinal tract and into the blood, fluids and tissues of the body. Alternatively, the medicament can be of any type of medication which acts through the buccal tissues of the mouth to transmit the active ingredient directly into the blood stream thus avoiding first liver metabolism and by the gastric and intestinal fluids which often have an adverse inactivating or destructive action on many active ingredients unless they are specifically protected against such fluids as means of an enteric coating or the like. The active ingredient can also be of a type of medication which can be transmitted into the blood circulation through the rectal tissues.

Representative active medicaments include antacids, antisubstances, coronary dilators, peripheral vasodilators, antipsychotropics, antimanics, stimulants, antihistamines, laxatives, decongestants, vitamins, gastrosedatives, antidiarrheal preparations, antidrugs, vasodilators, antiarrythmics, antidrugs, vasoconstrictors and migraine treatments, anticoagulants and antithrombiotic drugs, analgesics, antihypnotics, sedatives, anticonvulsants neuromuscular drugs, hyper and hypoglycaemic agents, thyroid and antithyroid preparations, diuretics, antispasmodics, uterine relaxants, mineral and nutritional additives, antiobesity drugs, anabolic drugs, erthropoietic drugs, antiasthematics, expectorants, cough suppressants, mucolytics, antiuricemic drugs, and drugs or substances acting locally in the mouth.

Typical active medicaments include gastrointestinal sedatives such as metoclopramide and propanthelline bromide, antacids such as aluminum trisilicate, aluminum hydroxide and cimetidine, antidrugs such as phenylbutazone, indomethacin, naproxen, ibuprofen, flurbiprofen, diclofenac, dexamethasone, prenisone and prednisolone, coronary vasodialotor drugs such as glyceryl trinitrate, isosorbide dinitrate and pentaerythritol tetranitrate, peripheral and cerebral vasodilators such as solctidilum, vincamine, naftidrofuryl oxalate, comesylate, cyclandelate, papaverine and nicotinic acid, antisubstances such as erythromycin, stearate, cephalexin, nalidixic acid, tetracycline hydrochloride, ampicillin, flucolaxacillin sodium, hexamine mandelate and hexamine hippurate, neuroleptic drugs such as fluazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrocholoride, imipramine and desmethylimipramine, central nervous stimulants such as methylphenidat, ephedrine, epinephrine, isoproterenol, amphetamine sulfate and amphetamine hydrochloride, antidrugs such as diphenhydramine, diphenylpyraline, chlorpheniramine and brompheniramine, antidiarrheal drugs such as bisacodyl and magnesium hydroxide, the laxative drug, dioctyl sodium sulfosuccinate, nutritional supplements such as dicyclomine and diphenoxylate drugs effecting the rhythm of the heart such as verapamil, nifedepine, diltiazem, procanamide, disopyramide, bretylium tosylate, quindine sulfate and qunidine gluconate, drugs used in the treatment of hypertension such as propranolol hydrochloride, guanethidine monosulphante, methyidopa, oxprenolol hydrochloride, captopril and hydralazine, drugs used in the treatment of migraine such as ergotamine, drugs effecting the coagulability of blood such as epsilon aminocaproic acid and protamine sulfate, analgesic drugs such as acetylsalicyclidic acid, acetaminophen, codeine phosphate, codeine sulfate, oxycodone, dihydrocodeine tartrate, oxydodeinone, morphine, heroin, nalbuphine, butorphanol tartrate, pentazocine hydrochloride, cyclazacine, pethidine, buprenorphine, scopolamine and mefenamic acid, antidrugs such as phenytoin sodium and sodium valproate, neuromuscular drugs such as dantrolene sodium, substances used in the treatment of diabetes, such as tolbutamide, diabenase glucagons and insulin, drugs use din the treatment of thyroid gland dysfunction such as triiodothyronine, liothyronine sodium, levothyroxine sodium and propylthiouracil, diuretic drugs, such as furosemide, chlorthalidone, hydrochlorthiazide, spironolactone and triampterene, the uterine relaxant drug ritodrine, appetite suppressants such as fenfluramine hydrochloride, phentermine and diethylproprion hydrochloride, antidrugs such as aminophylline, theophylline, salbutamol, oraciprenaline sulphate and terbutaline sulphate, expectorant drug such as guaiphenesin, cough suppressants such as dextromethorphan and noscapine, mucolytic drugs such as carbocisteine, antiseptics such as cetylpyridinium chloride, tyrothricin and chlorhexidine, decongestant drugs such as phenylpropanolamine and pseudoephedrine, hypnotic drugs such as dichloraphenazone and nitrazepam, antidrugs such as promethazine theociate, haemopoetic drugs such as ferrous sulphate, folic acid and calcium gluconate, uricosuric drugs such as sulphinpyrazine, allopurinol and probenecid and the like. It is understood that the invention is not restricted to the above medications.

The amount of pharmaceutically active ingredient in the present composition can vary widely, as desired. Preferably, the active ingredient is present in the composition in the range of about 0.001 to about 10 weight %. More preferably, the amount of active ingredient is present in the rage of about 0.001 to 5 weight %.

When the pharmaceutically active moiety is levothyroxine sodium or liothyronine sodium, the preferred amount of the active moiety in the composition is in the range of about 0.01 to 5 weight %. The more preferred range is from about 0.01 to 1.0 weight % levothyroxine. The minimum amount of levothyroxine can vary, so long as an effective amount is utilized to cause the desired pharmacological effect. Typically, the dosage forms have a content of levothyroxine in the range of about 25 to 300 micrograms.

The β-sheet microcrystalline cellulose product of the present invention is prepared by forming a wet cake, drying the cake with a drum dryer, then passing the dried product through a screen or mill for sizing which produces a β-sheet microcrystalline cellulose which has a flat needle shape, as disclosed in U.S. Pat. No. 5,574,150. Said β-sheet microcrystalline product can be prepared by Asahi Chemical of Japan and marketed by FMC Company of Newark, Del. under the trademark CEOLUS. The morphology and performance characteristics of the Ceolus product are different from those of other α-form microcellulose products (for example, Avicel and Emcocel), and are suitable for preparing the present stabilizing pharmaceutical composition.

The amount of β-sheet microcrystalline product used in the product composition is at least 50 weight % of the final composition. Preferably, the amount of β-sheet microcrystalline product is in the range of about 50 to 99 weight %. Most preferably, the amount of β-sheet microcrystalline product is in the range of about 60 to 90 weight % of the final composition.

Other suitable excipients for the present invention include fillers such as starch, alkaline inorganic salts such as trisodium phosphate, tricalcium phosphate, calcium sulfate and sodium or magnesium carbonate. The fillers can be present in the present composition in the range of about 0 to 50 weight %.

Suitable disintegrating agents include corn starch, crosslinked sodium carboxymethcellulose (croscarmellose) and cross-linked polyvinylpyrrolidone (crospovidone). A preferred disintegrating agent is croscarmellose. The amount of disintegrating agent used is in the range of about 0 to 50 weight %. Preferably, the disintegrating agent is in the range of about 10 to 40 weight %.

Suitable glidents for use in the present invention include colloidal silicon dioxide and talc. The amount of glident in the present composition is from about 0 to 5 weight %, and the preferred amount is about 0 to 2 weight %.

Suitable lubricants include magnesium and zinc stearate, sodium stearate fumarate and sodium and magnesium lauryl sulfate. A preferred lubricant is magnesium stearate. The amount of lubricant is typically in the range of about 0 to 5 weight %, preferably in the range of about 0.1 to 3 weight %.

The oral pharmaceutical product is prepared by thoroughly intermixing the active moiety and the β-sheet form of microcrystalline cellulose, along with other excipients to form the oral dosage. Food grade dyes can also be added. For example, it is common to distinguish dosages of various potency by the color characteristics of such dyes.

The stabilized oral dosages of thyroid hormone are prepared by forming a trituration of the active moiety (i.e. levothyroxine sodium and/or liothyronine sodium) and β-sheet microcrystalline cellulose. The trituration is blended with β-sheet microcrystalline cellulose and additional excipients and compressed into oral dosages.

Design of the tableting apparatus is critical to maintain consistency from one oral dosage to the next. The formulation batches are a blend of solid compositions of various shapes and sizes. Blending is used to achieve a measure of homogeneity. In particular the active thyroid moiety is desired to be evenly distributed throughout the batch. In a typical 400 kg batch, the amount of active moiety represents less than 1 kg of the total weight. For example, when producing 145 mg tablets with a 300 mcg dosage, approximately 0.8 kg of a 400 kg batch is the active moiety. In addition each tablet is to contain from 100% to 102.5% label claim potency (higher dosage levels may use a narrower 100% to 101% tolerance).

It is typical for compressible medicament tablets to be formed using a 2:1 fill to compression ratio. However, for medicamet tablets formed using the present invention a fill to compression ration from 3.3:1 to 4:1 is needed to obtain desired tablet density. This results from the β-sheet microcrystalline cellulose having a lower bulk density, as compared to other excipients.

Higher tablet density can be accomplished by adjusting a tableting machine to increase the compression ratio. Tableting machines are commonly known to practitioners in the art and include those available from Manesty and Stokes. It has been found that making such adjustments to the compression ratio results in poor tablet surface finish as well as inconsistent tablet weights.

Instead, the design of the tableting dies must be adjusted. It has been determined that during the filling of the tableting dies, a minimum of 5–6 mm die overfill. In most cases this requires replacement of the tableting dies with dies an additional 2–3 mm deep.

When using the extra-deep dies and a compression ratio of from 3.3:1 to 4.0:1 consistent weight tablets with good surface finish were produced.

EXAMPLES

Stability testing was performed on samples of the thyroid hormone drug formulation used in manufacturing tablets with an active moiety of levothyroxine sodium. Tests were performed on direct compression formulations for dosage strength of 25 mcg. Example 1 tablets comprise the β-sheet microcrystalline cellulose while Control 1 tablets comprise the traditional α-form microcrystalline cellulose. The composition of Example 1 and Control 1 tablets are presented in Table 1 and stability test results in Table 2:

TABLE 1

Tablet Formulation for 25 mcg Dosages of Levothyroxine Sodium

| Example 1 Tablet | Control 1 Tablet | Component |
| --- | --- | --- |
| 0.0297 mg | 0.0297 mg | Levothyroxine Sodium, USP |
| 108.55 mg | | β-sheet microcrystalline cellulose |
| | 108.55 mg | α-form microcrystalline cellulose |
| 35.079 mg | 35.079 mg | Croscarmellose Sodium, NF |
| | 0.352 mg | FD&C Yellow #6 16% (14–20%) |
| 1.018 mg | 1.018 mg | Magnesium Stearate, NF |
| 145.0 mg total | 145.0 mg total | |

TABLE 2

Stability Test - Potency at 25° C. -- % Label Claim

| Elapsed Time | 0 | 73 Days | 13 Months | 15 Months |
| --- | --- | --- | --- | --- |
| Example 1 Tablet | 106.4 | 105.5 | 104.4 | 102.9 |
| Example 1% Potency Loss | | 0.9% | 2.0% | 3.5% |
| Control 1 Tablet | 99.2 | 89.5 | 85.0 | 83.2 |
| Control 1% Potency Loss | | 2.7% | 14.2% | 16.0% |

As seen in Table 2, the stability of pharmaceutical formulations of the present invention are improved significantly by the use of the β-sheet microcrystalline cellulose. Potency loss of the present invention is 3.5% versus 16.0% potency loss experienced in a similar formulation with the α-form microcrystalline cellulose.

Tableting testing was performed on the formulation for Example 1 tablets. Initial results with standard die depths was a relative standard deviation of 2.2 to 3.5% tablet weight. With the use of the herein described extra deep tablet dies, the relative standard deviation is 1.2%. Testing was performed on a Manesty tableting machine with compression ratios from 3.3:1 to 4.0:1.

Tablet quality is also dependent upon the storage of the β-sheet microcrystalline cellulose. Best results are achieved when the cellulose is received in drums or portable containers instead of bags. The bag form suffers from compression during transportation from raw materials suppliers. Test result for tableting are presented in attached Exhibit A.

Additional examples of solid dosage formulations are illustrated in Tables 3 and 4. Stability testing data of these additional examples are illustrated in attached Exhibit B.

TABLE 3

Tablet Formulation for Dosages of Levothyroxine Sodium

| 25 mcg Dosage | 50 mcg Dosage | 75 mcg Dosage | Component |
| --- | --- | --- | --- |
| 0.025 mg/tablet | 0.0500 mg/tablet | 0.0750 mg/tablet | Levothyroxine sodium |
| 108.529 mg/tablet | 108.856 mg/tablet | 108.438 mg/tablet | β-sheet microcrystalline cellulose |
| 35.079 mg/tablet | 35.079 mg/tablet | 35.079 mg/tablet | Crosscarmellose sodium |
| 0.352 mg/tablet | | 0.383 mg/tablet | Food Grade Dye |
| 1.018 mg/tablet | 1.018 mg/tablet | 1.018 mg/tablet | Magnesium stearate |
| 145 mg/tablet | 145 mg/tablet | 145 mg/tablet | Total |

TABLE 4

Tablet Formulation for Dosages of Levothyroxine Sodium

| 100 mcg Dosage | 112 mcg Dosage | 300 mcg Dosage | Component |
| --- | --- | --- | --- |
| 0.100 mg/tablet | 0.112 mg/tablet | 0.300 mg/tablet | Levothyroxine sodium |
| 108.406 mg/tablet | 107.711 mg/tablet | 108.451 mg/tablet | β-sheet microcrystalline cellulose |
| 35.079 mg/tablet | 35.079 mg/tablet | 35.079 mg/tablet | Crosscarmellose sodium |
| 0.388 mg/tablet | 1.080 mg/tablet | 0.142 mg/tablet | Food Grade Dye |
| 1.018 mg/tablet | 1.018 mg/tablet | 1.018 mg/tablet | Magnesium stearate |
| 145 mg/tablet | 145 mg/tablet | 145 mg/tablet | Total |

While the present invention has been described in the context of preferred embodiments and examples, it will be readily apparent to those skilled in the art that other modifications and variations can be made therein without departing from the spirit or scope of the present invention. For example, the active moiety levothyroxine sodium can be changed to liothyronine sodium and similar products and still be considered as part of the claimed invention. Accordingly, it is not intended that the preferred embodiments and examples, but rather as being limited only by the scope of the invention as defined in the claims appended hereto.

Having described our invention, we claim:

1. A pharmaceutical composition in a solid dosage form comprising a thyroid hormone salt and a pharmaceutical filler, wherein said pharmaceutical composition (i) is suitable for oral consumption by a patient, (ii) is substantially free of excipients that can react with or degrade the thyroid hormone salt, and (iii) has a stable shelf life of up to about 18 months, and wherein the thyroid hormone salt loses no more than about 12.6% in potency during shelf life.

2. The pharmaceutical composition of claim 1, wherein said filler is a β-sheet form of microcrystalline and the β-sheet form of microcrystalline comprises at least about 50 weight % of said pharmaceutical composition by weight.

3. The pharmaceutical composition of claim 1, wherein the thyroid hormone salt is levothyroxine sodium.

4. The pharmaceutical composition of claim 2, wherein the thyroid hormone salt is levothyroxine sodium.

5. The pharmaceutical composition of claim 1, wherein the thyroid hormone salt is liothyronine sodium.

6. The pharmaceutical composition of claim 2, wherein the thyroid hormone salt is liothyronine sodium.

7. A method of preparing a solid dosage form suitable for oral administration comprised of a thyroid hormone salt, said method comprising blending the thyroid hormone salt and a pharmaceutical filler to form a blend, and forming the solid dosage form from the blend, wherein the thyroid hormone salt loses potency at a rate of no more than about 0.7% per month for a period of time equal to at least about 18 months, wherein said period of time begins on the date in which said solid dosage form is first blended, and wherein said solid dosage form is substantially free of excipients that can react with or degrade the thyroid hormone salt.

8. The method of claim 7, wherein the solid dosage is formed by compressing the blend in a tableting machine.

9. The method of claim 8, wherein the blend is compressed in a ratio of initial volume to final volume from 3.3:1 to 4.0:1.

10. The method of claim 7, wherein the thyroid hormone salt comprises levothyroxine sodium.

11. The method of claim 7, wherein the thyroid hormone salt comprises liothyronine sodium.

12. The method of claim 8, wherein the tableting machine further comprises extra deep tablet dies that maintain a free clearance of at least 3.0 mm during filling.

13. The method of claim 12, wherein the tableting machine forms tablets in a shape selected from the group consisting of cylindrical shape and raised violin shape.

14. The pharmaceutical composition of claim 1, wherein the thyroid hormone salt is an untreated levothyroxine sodium.

15. The pharmaceutical composition of claim 14, wherein the solid dosage form is a tablet.

16. The pharmaceutical composition of claim 14, wherein the excipient is lactose.

17. The pharmaceutical composition of claim 3, wherein the levothyroxine sodium is an untreated levothyroxine sodium.

18. The pharmaceutical composition of claim 17, wherein the solid dosage form is a tablet.

19. The pharmaceutical composition of claim 7, wherein the thyroid hormone salt is an untreated levothyroxine sodium.

20. The method of claim 19, wherein the solid dosage form is a tablet.

21. The method of claim 20, wherein the excipient is lactose.

22. The method of claim 10, wherein the levothyroxine sodium is an untreated levothyroxine sodium.

23. The method of claim 22, wherein the solid dosage form is a tablet.

24. The method of claim 23, wherein the excipient is lactose.

* * * * *